US012532930B1

(12) United States Patent
Jungsberger et al.

(10) Patent No.: US 12,532,930 B1
(45) Date of Patent: Jan. 27, 2026

(54) STABILIZED WEIGHT LIFTING BELT

(71) Applicant: Landau International Holdings LLC, Manasquan, NJ (US)

(72) Inventors: Peter J. Jungsberger, Manasquan, NJ (US); Larry Williams, Manasquan, NJ (US)

(73) Assignee: Landau International Holdings LLC, Manasquan, NJ (US)

( * ) Notice: Subject to any disclaimer, the term of this patent is extended or adjusted under 35 U.S.C. 154(b) by 0 days.

(21) Appl. No.: 19/291,228

(22) Filed: Aug. 5, 2025

(51) Int. Cl.
*A41F 9/00* (2006.01)
*A61F 5/02* (2006.01)

(52) U.S. Cl.
CPC .............. *A41F 9/002* (2013.01); *A61F 5/028* (2013.01)

(58) Field of Classification Search
CPC .......... A41F 9/002; A61F 5/028; A44B 11/00; A44B 11/065
See application file for complete search history.

(56) References Cited

U.S. PATENT DOCUMENTS 3,724,248 A * 4/1973 Obermann ........... H01H 43/102 74/122
4,179,945 A * 12/1979 Obermann ........... H01H 43/102 74/122
4,649,239 A * 3/1987 Duve ................... H01H 43/101 200/38 B
5,572,747 A * 11/1996 Cheng .................... A44B 11/12 2/322
5,673,463 A * 10/1997 Chih-wen ............ A44B 11/008 24/265 BC
5,749,127 A * 5/1998 Hsieh ................... A44B 11/006 24/3.13
5,752,298 A * 5/1998 Howell .................. A44B 11/12 2/418
5,887,318 A * 3/1999 Nicoletti ............ A43C 11/1413 24/71 SK
5,926,927 A * 7/1999 Winkler .................. A41F 1/008 24/593.1
6,067,692 A * 5/2000 Chang .................. A44B 11/008 24/303
6,148,485 A * 11/2000 Wu .................... A44B 11/2592 24/191
6,715,449 B1 * 4/2004 Jordan ................ A01K 27/005 24/DIG. 48
7,246,383 B2 * 7/2007 Musal .................... A44B 11/20 2/418
7,877,845 B2 * 2/2011 Signori ...................... F16B 2/08 24/68 SK
8,763,210 B2 * 7/2014 Vincent ..................... A43B 5/04 24/71 SK (Continued)

OTHER PUBLICATIONS

PR Powerlifting Belt™ for powerlifting, workouts, and powerbuilding—Inzer Advance Designs, https://inzer.com/products/pr-belt™, Jul. 3, 2025, 8 pages.

*Primary Examiner* — Richale L Quinn
(74) *Attorney, Agent, or Firm* — Martin Fessenmaier; Umberg Zipser LLP

(57) ABSTRACT

A weightlifting belt that mitigates or eliminates off-axis deformation and flexing is disclosed, the belt having a recessed T-shaped ratchet to form L-shaped engagement surfaces on one side of the strap, and the belt further having a buckle assembly with L-shaped rail elements and two pawls on the other side of the strap.

18 Claims, 6 Drawing Sheets

(56) References Cited

U.S. PATENT DOCUMENTS

| | | | | |
|---|---|---|---|---|
| 8,910,596 | B2 * | 12/2014 | Finlan | A01K 27/005 119/856 |
| 9,066,499 | B2 * | 6/2015 | McCarren | A44B 11/266 |
| 9,149,090 | B1 * | 10/2015 | Taylor | A44B 11/006 |
| 9,241,543 | B1 * | 1/2016 | Peng | A44B 11/12 |
| 9,277,776 | B2 * | 3/2016 | Laatz | A41F 9/002 |
| 9,351,526 | B1 * | 5/2016 | Taylor | A44B 11/125 |
| 9,351,539 | B2 * | 5/2016 | Briggs | A43C 11/1473 |
| 9,615,631 | B2 * | 4/2017 | Laatz | A44B 11/125 |
| 9,622,532 | B2 * | 4/2017 | Tryner | A42B 3/205 |
| 10,070,701 | B1 * | 9/2018 | Liu | A44B 11/125 |
| 10,794,664 | B1 * | 10/2020 | Moreno | F41C 33/046 |
| 10,952,509 | B2 * | 3/2021 | Simpson | B25H 3/00 |
| 11,864,638 | B2 * | 1/2024 | Kozak | A44C 5/2042 |
| 2007/0039426 | A1 * | 2/2007 | Chuang | B25B 23/1427 81/475 |
| 2013/0047388 | A1 * | 2/2013 | Kavarsky | A63C 10/06 24/68 E |
| 2013/0091674 | A1 * | 4/2013 | Chen | A43C 11/146 24/68 SK |
| 2013/0135547 | A1 * | 5/2013 | Hibayashi | G02F 1/133707 349/33 |
| 2016/0135547 | A1 * | 5/2016 | Kuffrey | B25H 3/00 482/93 |
| 2016/0183636 | A1 * | 6/2016 | Laatz | A41F 9/002 2/312 |
| 2016/0338451 | A1 * | 11/2016 | Scoffier | A44B 11/125 |
| 2019/0200711 | A1 * | 7/2019 | Simpson | A44B 11/125 |
| 2023/0397681 | A1 * | 12/2023 | Rolih | A41F 9/025 |
| 2024/0373962 | A1 * | 11/2024 | Goodwin | A44B 11/22 |

* cited by examiner

STABILIZED WEIGHT LIFTING BELT

All referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is weightlifting belts, especially as it relates to ratcheting belts comprising multiple engagement surfaces that cooperate to reduce off-axis flexing and deformation.

BACKGROUND

The following description includes information that may be useful in understanding the present invention. It is not an admission that any of the information provided herein is prior art or relevant to the presently claimed invention, or that any publication specifically or implicitly referenced is prior art.

Powerlifting belts help weightlifters by increasing thoracic pressure and to help brace the core muscles. The pressure on the abdomen improves stability and precision during lifts, which helps protect the weightlifter's spine and surrounding muscles. Powerlifting belts must be highly adjustable to be effective. Users should be able to precisely tighten the belt to support the core without restricting breathing. The correct tightness for a particular user may even vary depending on the lift being performed.

Many powerlifting belts rely on a conventional prong-based belt buckle. These buckles have limited adjustability based on the number and spacing of the holes in the belt. They are also cumbersome to use and secure under load and cannot be tightened or removed quickly.

Lever belts improve upon buckle-based belts by making it easier to tighten the belt under a heavy load. Lever belts, however, still have limited adjustability based on the number and spacing of holes in the belt. Users often find that their ideal tightness is in between holes.

Because of the limited adjustability, lever belts must come in a variety of sizes, thus making it difficult to share lever belts with other lifters with different waist sizes.

To address the issue of limited adjustability in prong-based belts and lever belts, some users have turned to ratcheting belts which typically offer more precise and incremental size adjustments for improved fit and comfort. However, ratcheting belts experience problems associated with stability. Specifically, these belts tend to suffer from off-axis flexing and deformation when worn, which reduces overall support when heavy lifting. For example, the belt of US20160135547A1 uses a ladder strap and ratcheting buckle system in which the belt is donned by pushing a strap into a buckle to the desired tightness, and the belt is loosened by operating the buckle to release the strap. Aside from engaging the buckle to the ladder, this disclosure does not describe any other mechanism for the buckle to engage or secure itself to the strap to ensure stability when worn. Therefore, this belt would flex or deform when worn unless it is configured to fit extremely tight against the user's body, which would be uncomfortable.

In another example, the belt of U.S. Pat. No. 10,794,664B1 is a ratcheting belt designed for carrying firearms and tactical gear, featuring a flexible strip, a ladder strap with teeth, and a ratchet assembly for adjustability. The belt's buckle secures onto the strap exclusively via a lever that grabs the teeth on the strap. Again, this patent does not describe any other mechanism for the buckle to engage or secure onto the strap, raising stability concerns. Engaging a buckle with the teeth is typically insufficient to fully support stability.

Similarly, the belts of U.S. Pat. No. 5,673,463A, US20230397681A1, Pioneer™ Stock 4_13 mm PAL V2 Lever Weight Belt-IN STOCK • LG (35_-44_), and Inzer® Advance Designs PR® Powerlifting Belt™ for powerlifting, workouts, and powerbuilding each lack additional mechanisms for stability apart from a buckle engaging with teeth. As a result, the Inzer® belt, for example, resorts to placing a metal clamp to hold the strap in place, which can be uncomfortable for the user because it presses against the user's belly when worn. Moreover, although the clamp attempts to address stability concerns, a metal clamp positioned on only one side of the belt when worn is insufficient to provide structural stability because it fails to evenly distribute forces across the belt's width, allowing the unsupported side to flex, twist, or deform under tension, thereby compromising overall rigidity and support.

Thus, there is still a need for belts with improved stability that mitigate or eliminate the issue of off-axis deformation while still allowing adjustability.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY OF THE INVENTION

The inventive subject matter provides devices and methods in which a belt, typically used for weightlifting, reduces off-axis deformation and/or flexing.

For example, in one embodiment of the inventive subject matter, a device is contemplated comprising a belt comprising a strap having a first end and a second end, wherein a recess is formed in the first end, wherein the recess comprises opposite walls; a T-shaped ratchet at least partially disposed in the recess, thereby forming with the opposite walls of the recess respective L-shaped engagement surfaces; a buckle assembly coupled to the second end, wherein the buckle assembly comprises L-shaped rail elements configured to longitudinally and slidably engage with the L-shaped engagement surfaces, wherein the L-shaped rail elements are configured to engage with the L-shaped engagement surfaces to prevent off-axis deformation between the first end and the second end when the buckle assembly is coupled to the T-shaped ratchet; and wherein the buckle assembly further comprises a first pawl and a second pawl, wherein the first pawl is configured to allow incremental movement of the first pawl across the ratchet to thereby tighten the belt, and wherein the second pawl is configured to prevent movement of the buckle assembly when engaged to thereby prevent loosening of the belt.

In some embodiments, this device further comprises a tightening lever operably coupled to the first pawl, and moveable between a first position and a second position and wherein movement from the first position to the second position moves the first pawl by no more than two teeth of the ratchet.

In a different embodiment, this devices comprises a release lever operably coupled to the second pawl, and moveable from a first position and a second position and wherein movement form the first position to the second position disengages the second pawl from the ratchet.

In certain embodiments, the T-shaped ratchet comprises 90 degree angles.

However, in other embodiments, the T-shaped ratchet comprises non-right angles.

The T-shaped ratchet may comprise an opening embedded within the borders of the ratchet that span longitudinally across the ratchet in some embodiments.

In one optional aspect of the disclosed invention, the L-shaped engagement surfaces are textured.

In another aspect, the T-shaped ratchet comprises between 5 and 30 teeth.

The teeth may, in some such aspects, be equidistantly spaced from one another along the ratchet.

However, it should be appreciated that the teeth may be spaced at variable intervals.

In some embodiments of the contemplated subject matter, the strap comprises a rigid material.

In certain embodiments, the strap comprises leather.

And in different embodiments, the strap has a length between 90 centimeters and 120 centimeters.

In yet further different embodiments, the belt is about 10 centimeters wide and about 13 millimeters thick.

Viewed from another perspective, the instant invention is contemplated to include a method of reducing off-axis deformation in a belt, the method comprising: forming L-shaped engagement surfaces on a first end of the belt by coupling a T-shaped ratchet to a recess formed on the first end of the belt, wherein the recess comprises opposite walls; coupling a buckle assembly to the second end, wherein the buckle assembly comprises L-shaped rail elements configured to longitudinally and slidably engage with the L-shaped engagement surfaces; wherein the L-shaped rail elements are configured to engage with the L-shaped engagement surfaces to prevent off-axis deformation between the first end and the second end when the buckle assembly is coupled to the T-shaped ratchet; and wherein the buckle assembly further comprises a first pawl and a second pawl, wherein the first pawl is configured to allow incremental movement of the first pawl across the ratchet to thereby tighten the belt, and wherein the second pawl is configured to prevent movement of the buckle assembly when engaged to thereby prevent loosening of the belt.

In some optional embodiments of this method, the T-shaped ratchet comprises between 5 and 30 teeth.

In other embodiments, the teeth are equidistantly spaced from one another.

Yet, in some embodiments, the teeth are spaced at variable intervals.

Additionally, and in further embodiments, the method further comprises a step of operably coupling a tightening lever to the first pawl.

In still other embodiments, the method may involve a step of operably coupling a release lever to the second pawl.

Various objects, features, aspects and advantages of the inventive subject matter will become more apparent from the following detailed description of preferred embodiments, along with the accompanying drawing figures in which like numerals represent like components.

DETAILED DESCRIPTION

Traditional ratcheting belts, especially in the field of powerlifting and heavy lifting, suffer from instability when worn. Namely, these belts are known to be susceptible to off-axis flexing or deformation. Off-axis deformation may refer to the belt bending, flexing, or distorting in a direction that is not aligned with its intended path of tension, especially between a first end and a second end of the belt. This deformation will typically result in the body of the belt deviating from a flat or planar configuration along the waistline when worn, resulting in buckling, sagging, twisting, or curvature that comprises the uniform contact of the belt to the user's body. In some embodiments, off-axis deformation may be defined as displacement of the belt in a direction perpendicular to the circumferential plane of a user's waist, exceeding approximately 10, 15, 20, 25, or 30 degrees, and resulting in localized sagging or bowing.

While some belts have attempted to address this problem by placing metal clamps around the belt to hold it in place, such solutions fail to maintain consistent structural rigidity due to the lack of full width support and uniform constraint across the belt. Additionally, a metal clamp wrapped around the belt would cause discomfort to the user, as the metal would press against the user's belly or waist when worn.

Remarkably, the instant disclosure identifies a novel belt that addresses the problem of off-axis flexing and deformation and thus offers superior stability over those known in the art. It is generally contemplated herein that the belt comprises multiple engagement surfaces that cooperate to reduce off-axis flexing and deformation when engaged simultaneously.

Figure 4:
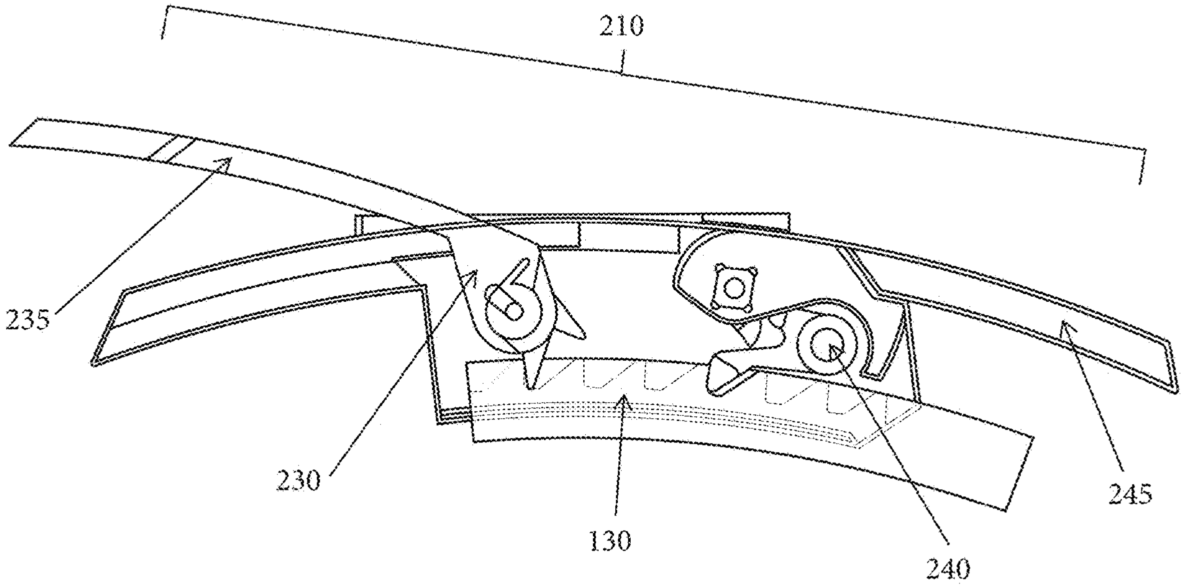
FIG. 4 depicts an exemplary side sectional view of the buckle assembly engaged with the teeth of the ratchet, wherein a first pawl and a second pawl are shown to be engaged with the teeth.
Figure 5:
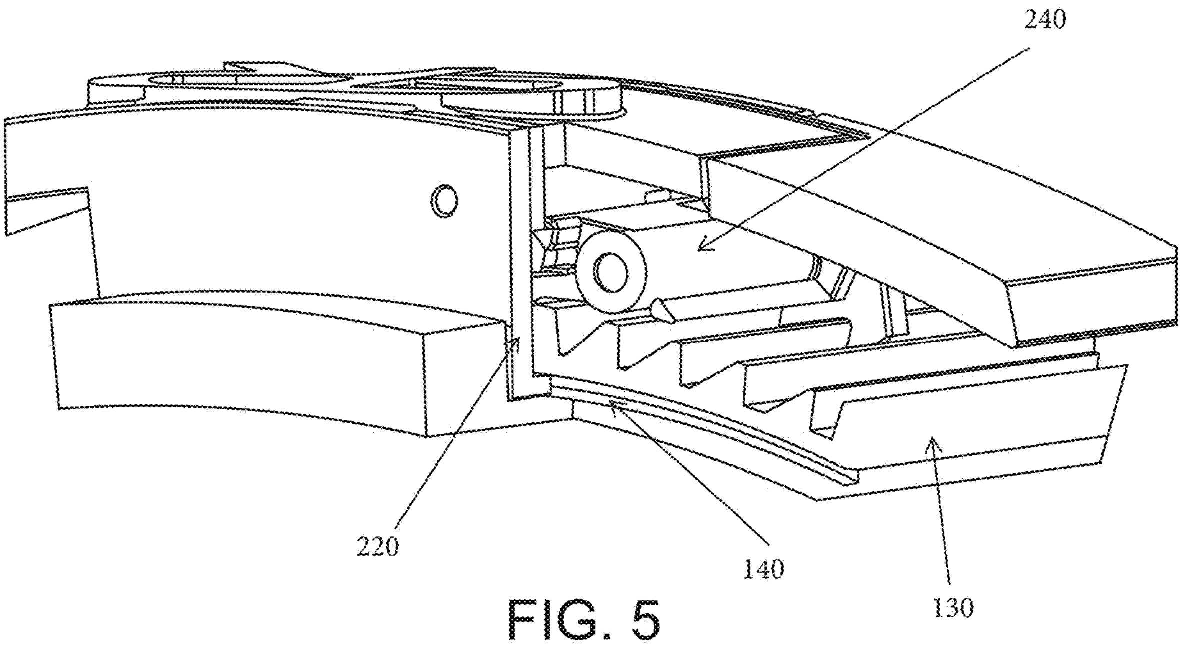
FIG. 5 depicts an exemplary perspective view of the buckle assembly engaged with the ratchet, clearly showing the L-shaped rail elements engaged with the L-shaped engagement surfaces.
Figure 6:
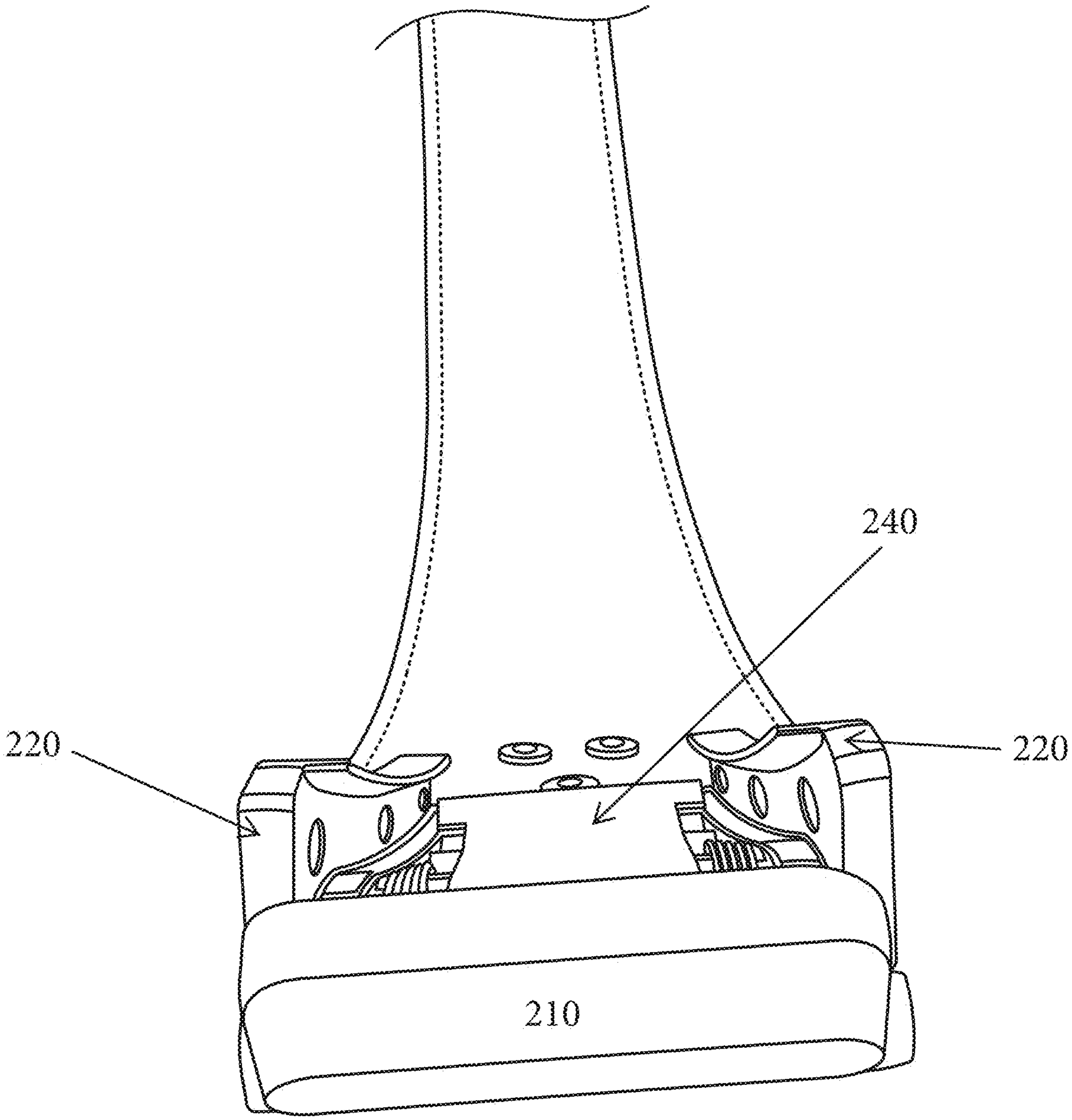
FIG. 6 depicts an exemplary perspective view of the second end of the belt exposing the L-shaped rail elements on either side of the buckle assembly.

For example, and in one embodiment of the inventive subject matter, a belt is contemplated comprising a first end 100 and a second end 200, wherein a recess 110 is formed in the first end 100, wherein the recess 110 comprises opposite walls 120; a T-shaped ratchet 130 at least partially disposed in the recess 110, thereby forming with the opposite walls 120 of the recess 110 respective L-shaped engagement surfaces 140; a buckle assembly 210 coupled to the second end 200, wherein the buckle assembly 210 comprises L-shaped rail elements 220 that can longitudinally and slidably engage with the L-shaped engagement surfaces 140, wherein the L-shaped rail elements 220 are configured to engage with the L-shaped engagement surfaces 140 to prevent off-axis deformation between the first end 100 and the second end 200 when the buckle assembly 210 is coupled to the T-shaped ratchet 130; and wherein the buckle assembly 210 further comprises a first pawl 230 and a second pawl 240, wherein the first pawl 230 is configured to allow incremental movement of the first pawl 230 across the T-shaped ratchet 130 to thereby tighten the belt, and wherein the second pawl 240 is configured to prevent movement of the buckle assembly 210 when engaged to thereby prevent loosening of the belt. See FIG. 1 for a perspective view of the belt showing the first end 100 and the second end 200 and various components. See FIG. 4 for a perspective view of the pawls 230, 240 of the buckle assembly 210 on the T-shaped ratchet 130.

It is contemplated that the buckle assembly's 210 engagement with the engagement surfaces 140, together with the functions of the first pawl 230 and the second pawl 240, may cooperate as a system to provide a worn belt with enhanced stability, especially by reducing or eliminating off-axis deformation. This belt eliminates the need for a metal clamp placed at the front of the worn belt. For example, when the rail elements 220 of the buckle assembly 210 longitudinally and slidably engage the engagement surfaces 140, and the first pawl 230 and the second pawl 240 are in a locked position, such as when they engage respective teeth on the ratchet, it is contemplated that any tension, stress, or force applied to the belt will be substantially incapable of flexing or deforming the belt in a direction facing the ground.

It should be appreciated that the L-shaped engagement surfaces 140 and/or the T-shaped ratchet 130 need not be composed of strictly linear elements or form a perfect right angle. Therefore, "L-shaped" as used to describe L-shaped engagement surfaces 140 may be loosely L-shaped, roughly L-shaped, approximately L-shaped, L-like in shape, L-shaped with irregular angles, L-shaped though curved or uneven, mostly L-shaped but having protrusions, indentations, or textures, and/or any other variation of L-shaped. Further, the L-shaped engagement surfaces 140 may comprise perfect 90 degree angles or may comprise non-right angles, or a combination thereof. Similarly, "T-shaped" as used to describe the T-shaped ratchet 130 may be loosely T-shaped, roughly T-shaped, approximately T-shaped, T-like in shape, T-shaped with irregular angles, T-shaped though curved or uneven, mostly T-shaped but having protrusions, indentations, or textures, and/or any other variation of T-shaped. Further, the T-shaped ratchet 130 may comprise perfect 90 degree angles, or may comprise non-right angles, or a combination thereof. Additionally, or alternatively, the L-shaped engagement surfaces 140 and/or T-shaped ratchet 130 may be shaped entirely differently so long as the buckle assembly 210 has correspondingly-shaped rail elements 220 that can longitudinally and slidably engage the engagement surfaces 140.

Figure 3:
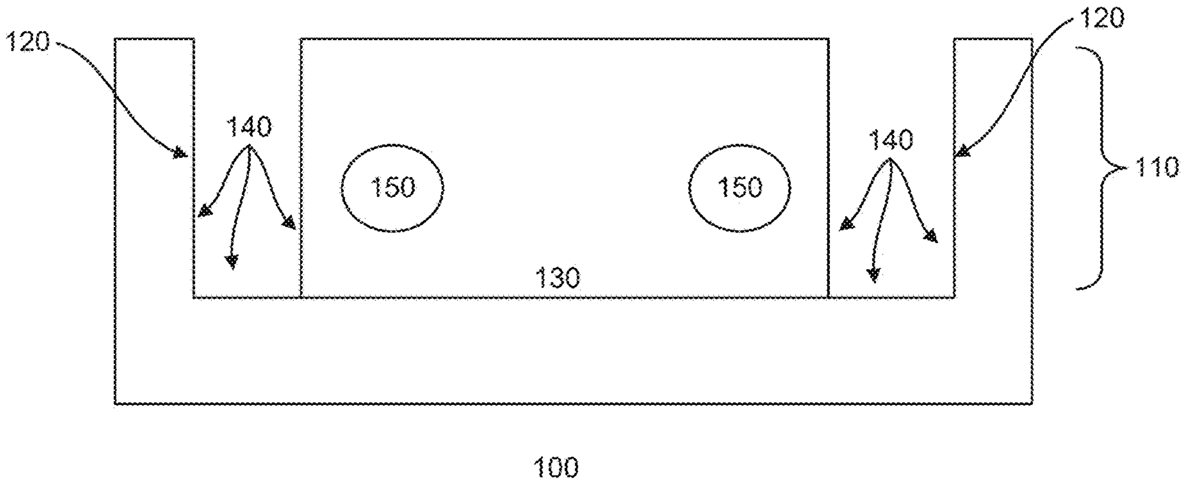
FIG. 3 depicts an exemplary simplified front view of a rectangular-shaped ratchet, wherein circular openings are disposed within the borders of the ratchet.

For example, and in further embodiments, the ratchet 130 may be a rectangular box-like structure or cuboid. However, in such embodiments, the engagement surfaces 140 would be rectangular. Because rectangular-shaped engagement surfaces may provide less stability than L-shaped engagement surfaces when engaged by correspondingly-shaped rail elements, it is typically preferred in such embodiments that the ratchet has additional engagement mechanisms. For example, the ratchet may have one or more cylindrical or rectangular openings 150 embedded within the borders of the ratchet 130 that span longitudinally across the ratchet 130, while the rail elements have corresponding structures to engage such openings 150. See FIG. 3. It should be appreciated that even the T-shaped ratchet 130 may have such openings 150 if desired.

In additional embodiments, it is contemplated that to maximize stability, the T-shaped design may include curved edges such that the rail elements 220 may hook the T-shaped structure. This design may enable better structural integrity as opposed to if the rail elements 220 merely contacted the engagement surfaces 140. For example, the top surface of the "T" may not be horizontal, but rather flare downward on either side, or even flare upward. In such cases, the corresponding rail elements 220 can have a curved shape themselves and hook onto the T-shape.

In most embodiments, the ratchet 130 comprises a plurality of teeth. It is typically contemplated that the ratchet 130 have anywhere from 5 to 30 teeth, and preferably 20, 21, 22, 23, or 25 teeth for some purposes. In such embodiments, the first pawl 230 and the second pawl 240 may move along the ratchet 130 by engaging respective teeth. In this context, engaging the teeth may describe any manner of catching one of the teeth such that the buckle assembly 210 cannot be easily displaced from its position.

The first pawl 230 is contemplated to move incrementally across the ratchet 130. For example, the first pawl 230 may be a pivoting pawl configured to engage sequential ratchet teeth in a stepwise manner, enabling motion of the buckle assembly 210 across the ratchet 130 in steps by locking and releasing as the first pawl 230 advances. The first pawl 230 may therefore be any type of pawl capable of pivoting, rotating, or walking across the teeth, especially by engaging various teeth as it advances along the ratchet 130. In some aspects, the pawl may be a one-way engaging pawl operable to step over successive teeth and lock during forward motion. In further embodiments, the first pawl 230 may be spring-based.

In certain embodiments, a tightening lever 235 may be operably coupled to the first pawl 230, wherein activating the tightening lever 235 causes the buckle assembly 210 to move along the ratchet 130 longitudinally. See FIG. 4. Activating the tightening lever may involve pulling it, pushing it, applying pressure, pressing a button, rotating or turning it, cranking it, flipping it, and/or pulling a trigger, and/or any other suitable means for activating a lever. Upon activating the tightening lever, the lever motion may induce the pawl to pivot or rotate, allowing it to engage the next adjacent tooth of the ratchet 130.

In other embodiments of the contemplated subject matter, a release lever 245 may be operably coupled to the second pawl 240, and activating the release lever 245 may cause the second pawl 240 to retract away from the ratchet 130. See FIG. 4. For example, the second pawl 240 may be an angled tongue that hangs beneath the buckle assembly 210. Because the buckle assembly 210 is typically positioned above the ratchet 130, this angled tongue can hook in between different teeth on the ratchet 130 in a manner that prevents the buckle assembly 210 from moving further. However, when the release lever is activated, this angled tongue may retract away from the teeth such that it is no longer hooked between any of the teeth, thus allowing the buckle assembly 210 to freely slide in either direction.

In further embodiments, the teeth of the ratchet 130 can span the entire width and/or length of the belt, the recess 110, or just a portion of the width and/or length of the belt or recess 110. The spacing of the teeth can vary. For example, in some embodiments, the teeth are spaced minimally according to their size and shape to allow for maximum adjustability. In further embodiments, the teeth may be equidistantly spaced from one another along the ratchet body, ensuring consistent angular displacement with each actuation of the pawl. However, alternatively, the teeth may be spaced at variable intervals, with certain regions having tighter or looser spacing to achieve a differentiated mechanical response. Selective spacing of the teeth may allow for different zones such as a high-engagement area for fine control (with smaller spacing) and a low-engagement area for rapid advancement (with larger spacing).

It is further contemplated that there may be, in some embodiments, two sets of rail elements corresponding to two sets of engagement surfaces. The first set of engagement surfaces are represented by the space defined by the opposite walls of the strap which face inward toward the center of the strap. The first set of rail elements on the buckle correspond to the first set of engagement surfaces, slidably engaging them. This engagement of the first set of rail elements with the first set of engagement surfaces prevents deformation and flexing side-to-side. It is contemplated that the length of the first set of rail elements, in certain embodiments, is contemplated to be approximately ⅓ the length of the first set of engagement surfaces. For example, in some embodiments, the length of the first set of rail elements is approximately 5 centimeters, 6 centimeters, 7 centimeters, 8 centimeters, 9 centimeters, 10 centimeters, 11 centimeters, 12 centimeters, or longer, while the corresponding first set of engagement surfaces have a length of 15 centimeters, 16 centimeters, 17, centimeters, 18 centimeters, 19 centimeters, 20 centimeters, 21 centimeters, 22 centimeters, or longer. Alternatively, the first set of rail elements may be ¼, ⅛, 1/16, or 1/32 the length of the first set of engagement surfaces, especially in embodiments where graded adjustability is preferred over stability. In other embodiments, the first set of rail elements may be ½ or ¾ the length of the first set of engagement surfaces, especially where maximum stability is prioritized. Regardless of the relative lengths of the first set of engagement surfaces and rail elements, it should be appreciated that less than the entire length of the rail elements can engage the engagement surfaces and still be securely engaged with the support of the pawls.

In yet further embodiments, the second set of engagement surfaces are represented by the space underneath the teeth which extends longitudinally. Thus, the second set of rail elements corresponds to and engages with the second set of engagement surfaces. This engagement between the respective second sets prevents any upward lift of the engaged buckle away from the teeth. It is contemplated in further embodiments that the second set of rail elements may have approximately the same lengths as the first set of rail elements, and the second set of engagement surfaces may have approximately the same lengths as the first set of engagement surfaces, and the ratio of lengths between the second sets of engagement surfaces to the second set of rail elements may be the same ratios as between the first sets.

However, while it is typically contemplated that the first set of rail elements have substantially the same lengths as the second set of rail elements, the first set of rail elements may be 5%, 10%, 15%, 20%, or 25% longer than the second set of rail elements.

The cooperation between the engagements between the first sets and the engagements between the seconds sets is contemplated to maximize stability of the belt and minimize off-axis deformation and flexing, especially because the aggregate engagements prevent both side-to-side and upward deformation.

Viewed from a different perspective, the contemplated belt may be a belt comprising a strap comprising (1) a plurality of teeth and (2) two or more channels; and a buckle assembly comprising: (1) a body, wherein the body is affixed to one end of the strap; (2) a spring-loaded locking means, wherein the spring-loaded locking means engages with at least one of the plurality of teeth; (3) a release lever, wherein the release lever is attached to the body and connected to the spring-loaded locking means, and wherein activating the release lever disengages the spring-loaded locking means from the plurality of rigid teeth; (4) a tightening lever comprising at least one ratchet prong, wherein the tightening lever is coupled to the body; (5) a ratchet wheel, wherein activating the ratchet wheel causes the at least one ratchet prong to engage with at least one of the plurality of teeth; (6) a first depression adjacent to the plurality of teeth; (7) a second depression underneath the teeth; wherein the first depression is substantially perpendicular to the second depression; and wherein the body of the buckle assembly is configured to be received within the first depression and the second depression Viewed from yet another perspective, it is contemplated that the belt may be a ratcheting powerlifting belt comprising a strap comprising: (1) a plurality of rigid teeth; and (2) two or more channels; and a buckle assembly comprising: (1) a body, wherein of the body is affixed to one end of the strap; (2) a spring-loaded locking means, wherein the spring-loaded locking means engages with at least one of the plurality of rigid teeth when locked; (3) a release lever, wherein the release lever is attached to the body and connected to the spring-loaded locking means, and wherein activating the release lever disengages the spring-loaded locking means from the plurality of rigid teeth; (4) a tightening lever comprising at least one ratchet prong, wherein the tightening lever is attached to the body, and wherein activating the ratchet wheel causes the at least one ratchet prong to engage with at least one of the plurality of rigid teeth; and (5) two or more right angle members, wherein each of the right angle members is arranged to fit into a respective channel of the two or more channels.

Viewed from a different perspective, it is contemplated that the belt may be a belt comprising an outer surface, wherein a recess is disposed within an intermediate region of the outer surface; a linear ratchet disposed within the recess, wherein the recess comprises opposing boundary surfaces that face the linear ratchet, wherein a first set of gaps are defined between each of the boundary surfaces and the linear ratchet; wherein the linear ratchet comprises overhanging portions, wherein a second set of gaps are defined between the overhanging portions and the bottom surface of the recess; wherein the linear ratchet comprises a plurality of teeth; and a buckle assembly comprising: (1) a body affixed to one end of the belt; (2) two right angle members, wherein each of the right angle members are arranged to fit into at least one gap in the first set of gaps and at least one gap in the second set of gaps; (3) a first pawl configured to engage with one of the plurality of teeth; and (4) a second pawl configured to engage with one of the plurality of teeth when the belt is in a locked position.

It should be appreciated that any of the elements described in such alternative embodiments may, individually or in any combination, be freely interchanged, combined, or incorporated with other embodiments as desired. For example, the spring-loaded locking means may be incorporated into embodiments previously described without reference to a spring-loaded means.

In further embodiments, it is contemplated that the belt and various components of the belt, such as the ratchet 130 or the teeth of the ratchet 130, may be made from any suitable material, but preferably a rigid material. A rigid material may describe any material that maintains structural integrity under compressive and tensile forces and resists deformation when subjected to pressure or bracing during lifting. Such materials are contemplated to provide consistent support to the torso and core, and may include, but are not limited to, leather, metal, rubber, polymers, nylon, and/or combinations thereof. For example, while the body of the belt may be made of a thick leather, the ratchet 130 may be made from a high-density nylon composite or a plastic, and the pawls may be made from metal. However, any variations or substitutions may be made to the foregoing example according to the instant disclosure.

It is further contemplated that the belts described herein are typically used as powerlifting belts, weightlifting belts, dip belts, back support belts, wrestling belts, boxing belts, and/or MMA belts, but several other suitable uses are contemplated. For example, the belts described herein may be suitable as casual belts, dress belts, tool belts, tactical belts, firearm belts, survival belts, yoga strap belts, martial arts belts, maternity belts, adult roleplay belts, ski belts, and/or pet collars, or any other types of belts.

The contemplated belts may have any suitable dimensions. In some contexts, such as when adhering the belt to the standards required by the International Powerlifting Federation (IPF), the belt's dimensions may be adapted for that purpose. For example, IPF standards typically require belts that are 10 centimeters wide and 13 millimeters thick. However, any other dimensions set by IPF are suitable. The contemplated belts can have any other suitable dimensions, such as 5.08 centimeters (2 inches), 7.62 centimeters (3 inches), 10.16 centimeters (4 inches), 12.7 centimeters (5 inches), or 15.24 centimeters (6 inches) wide, or any other value. Similarly, the belt can vary in thickness, such as 8 millimeters, 9 millimeters, 10 millimeters, 11 millimeters, 12 millimeters, 13 millimeters, 14 millimeters, 15 millimeters, or 16 millimeters thick.

In further embodiments, the strap of the belt may have a length of between 90 centimeters to 120 centimeters. Alternatively, the strap of the belt may have a length falling within one of the following ranges: 50 to 75 centimeters, 50 to 100 centimeters, 75 to 100 centimeters, 75 to 125 centimeters, 100 to 125 centimeters, or 100 to 150 centimeters.

In addition to reducing, mitigating, and/or eliminating off-axis deformation and flexing, several advantages of the described devices and belts are contemplated. For example, compared to traditional belts known in the art, the belts described herein reduce back pain and muscular tension while exercising, allowing a user to, for example, perform at least 2, 3, 4, 5, or even 6 times more squats before experiencing a pain/discomfort of 7 points or lower on the VAS scale. Any other exercise is applicable in addition to or as an alternative to squats.

It is further contemplated that off-axis deformation or flexing as seen in belts in the prior art will cause edge rolling over time. Edge rolling typically refers to the gradual curling, peeling, or deformation of a belt's edges away from the user's body due to repeated off-axis stress or flexion over time. This typically occurs when the belt is subjected to uneven forces, bending, or torsional pressure, causing the edges to lose their flat profile and roll outward or inward, reducing comfort, support, and longevity. The belts contemplated herein reduce edge rolling significantly. A belt known in the art, such as the Inzer belt described herein, is contemplated to have at least 15%, 30%, 45%, or even 60% more edge distortion over a period of one year, two years, or three years of common use as compared to the belts herein. Edge distortion can be measured by the percentage of area of the belt that shows edge rolling beyond a given threshold. Alternatively, edge rolling can be measured by the angle to which the edge curls away from the user's body.

It is further contemplated that the stability offered by the belts and devices described herein significantly reduce risk of injury while exercising. For example, and especially due to the stable engagement of each end of the straps to one another, and especially when made with a rigid material such as a polymer, these belts offer biomechanical support, reduce spinal shear and stress, reduce muscle activation in vulnerable areas such as the lower back, and cue the user to assume proper form. Further, wearing the belts contemplated herein increase the maximum load tolerance for users.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The foregoing discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
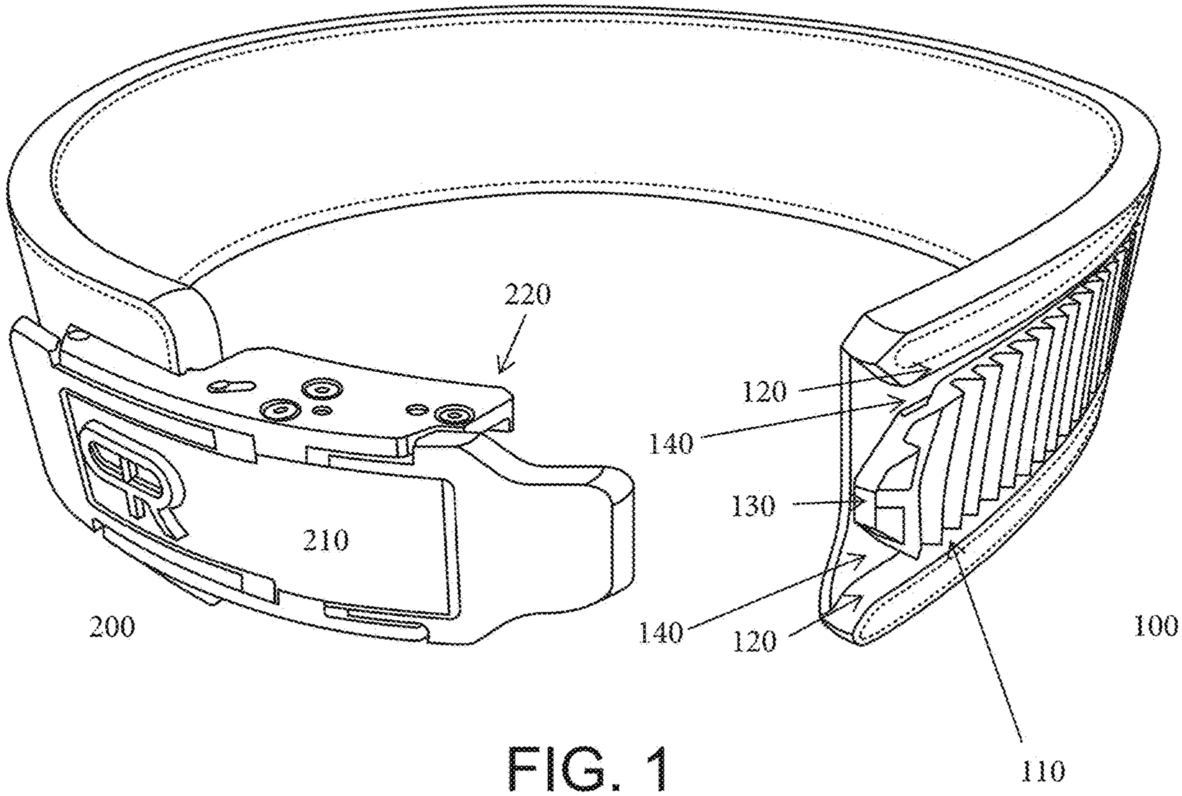
FIG. 1 depicts an exemplary perspective view of the contemplated belt showing a T-shaped ratchet recessed into the first end, and a buckle assembly coupled to the second end.
Figure 2:
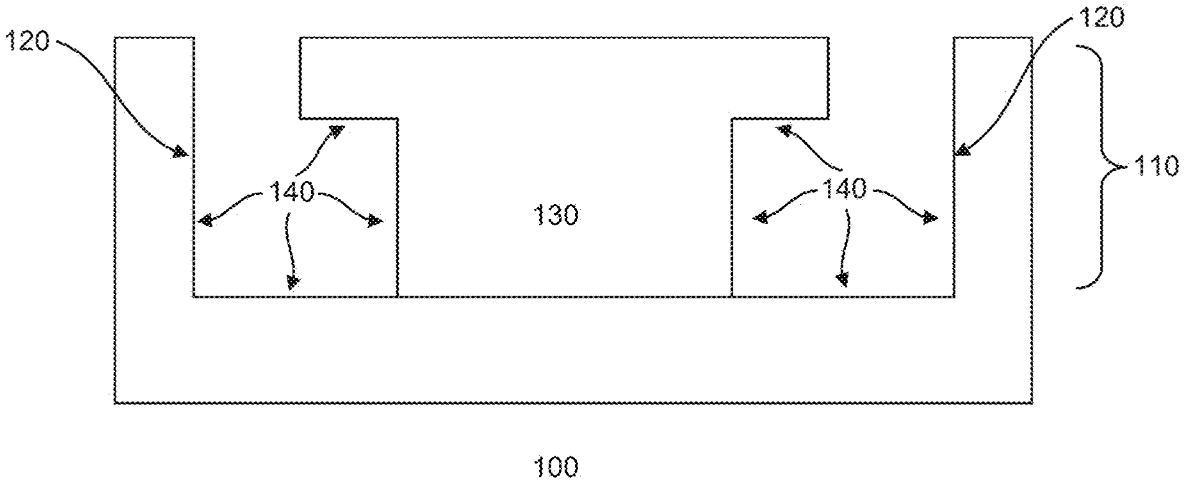
FIG. 2 depicts an exemplary simplified front view of the recessed T-shaped ratchet and the L-shaped engagement surfaces formed by such recessed T-shaped ratchet.

With respect to the remaining numerals in FIG. 2, the same considerations for like components with like numerals of FIG. 1 apply.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device, comprising:

a belt comprising a strap having a first end and a second end, wherein a recess is formed in the first end, wherein the recess comprises opposite walls;

a T-shaped ratchet at least partially disposed in the recess, thereby forming with the opposite walls of the recess respective L-shaped engagement surfaces;

wherein the T-shaped ratchet comprises an opening embedded within the borders of the ratchet that span longitudinally across the ratchet;

a buckle assembly coupled to the second end, wherein the buckle assembly comprises L-shaped rail elements configured to longitudinally and slidably engage with the L-shaped engagement surfaces, wherein the L-shaped rail elements are configured to engage with the L-shaped engagement surfaces to prevent off-axis deformation between the first end and the second end when the buckle assembly is coupled to the T-shaped ratchet; and wherein the buckle assembly further comprises a first pawl and a second pawl, wherein the first pawl is configured to allow incremental movement of the first pawl across the ratchet to thereby tighten the belt, and wherein the second pawl is configured to prevent movement of the buckle assembly when engaged to thereby prevent loosening of the belt.

2. The device of claim 1, further comprising a tightening lever operably coupled to the first pawl, and moveable between a first position and a second position and wherein movement from the first position to the second position moves the first pawl by no more than two teeth of the ratchet.

3. The device of claim 1, further comprising a release lever operably coupled to the second pawl, and moveable from a first position and a second position and wherein movement form the first position to the second position disengages the second pawl from the ratchet.

4. The device of claim 1, wherein the T-shaped ratchet comprises 90 degree angles.

5. The device of claim 1, wherein the T-shaped ratchet comprises non-right angles.

6. The device of claim 1, wherein the T-shaped ratchet comprises between 5 and 30 teeth.

7. The belt of claim 6, wherein the teeth are equidistantly spaced from one another along the ratchet.

8. The belt of claim 6, wherein the teeth are spaced at variable intervals.

9. The device of claim 1, wherein the strap comprises a rigid material.

10. The device of claim 1, wherein the strap comprises leather.

11. The device of claim 1, wherein the strap has a length between 90 centimeters and 120 centimeters.

12. The device of claim 1, wherein the belt is 10 centimeters wide and 13 millimeters thick.

13. A method of reducing off-axis deformation in a belt, the method comprising:

forming L-shaped engagement surfaces on a first end of the belt by coupling a T-shaped ratchet to a recess formed on the first end of the belt, wherein the recess comprises opposite walls, and wherein the T-shaped ratchet comprises an opening embedded within the borders of the ratchet that span longitudinally across the ratchet;

coupling a buckle assembly to the second end, wherein the buckle assembly comprises L-shaped rail elements configured to longitudinally and slidably engage with the L-shaped engagement surfaces;

wherein the L-shaped rail elements are configured to engage with the L-shaped engagement surfaces to prevent off-axis deformation between the first end and the second end when the buckle assembly is coupled to the T-shaped ratchet; and wherein the buckle assembly further comprises a first pawl and a second pawl, wherein the first pawl is configured to allow incremental movement of the first pawl across the ratchet to thereby tighten the belt, and wherein the second pawl is configured to prevent movement of the buckle assembly when engaged to thereby prevent loosening of the belt.

14. The method of claim 13, wherein the T-shaped ratchet comprises between 5 and 30 teeth.

15. The method of claim 14, wherein the teeth are equidistantly spaced from one another.

16. The method of claim 14, wherein the teeth are spaced at variable intervals.

17. The method of claim 13, further comprising a step of operably coupling a tightening lever to the first pawl.

18. The method of claim 13, further comprising a step of operably coupling a release lever to the second pawl.

* * * * *